March 28, 1939. J. GAUJARD Plant Pat. 321
ROSE
Filed May 5, 1937
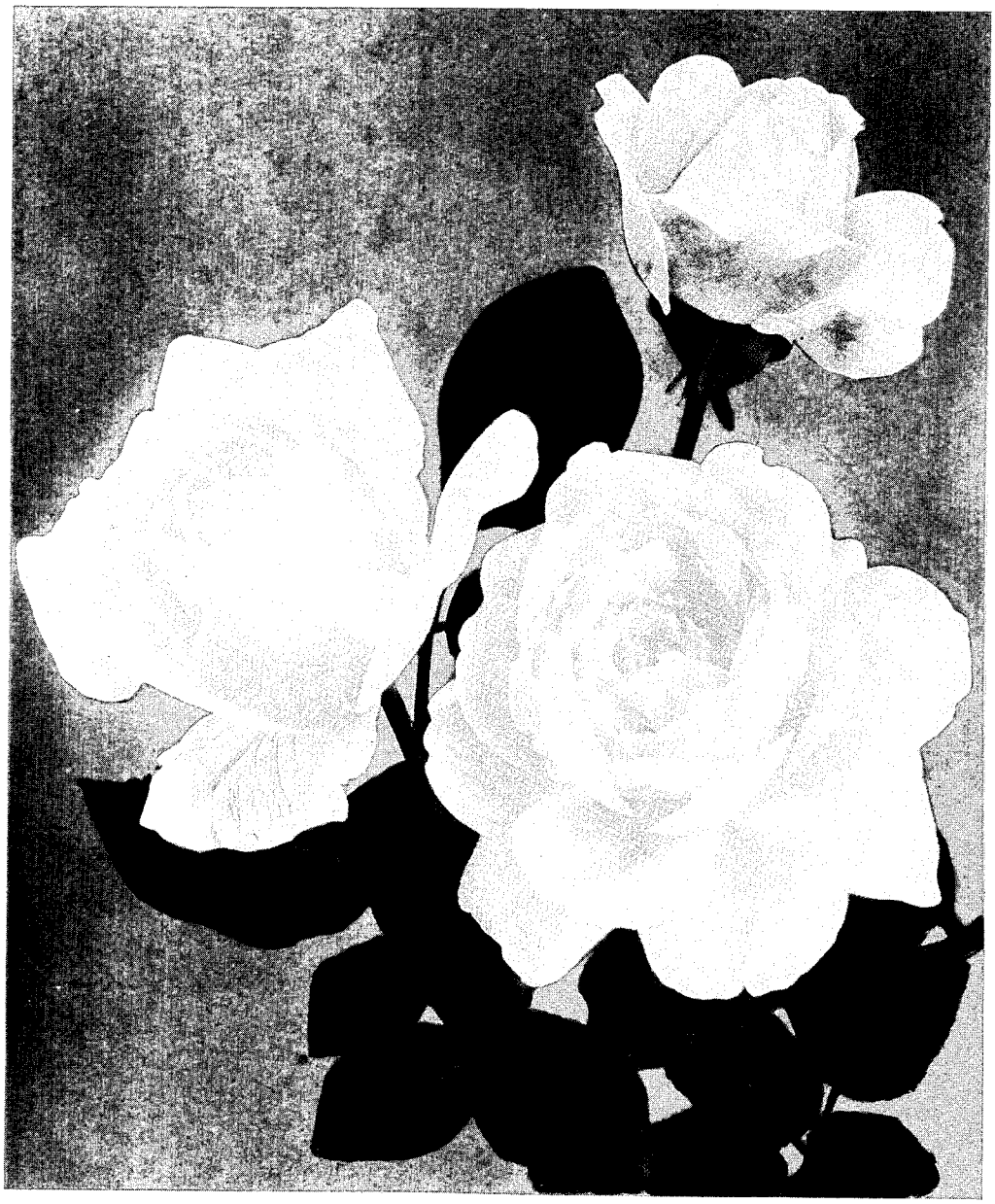
Inventor
Jean Gaujard
By Robert Robb
Attorney Patented Mar. 28, 1939

UNITED STATES PATENT OFFICE

321

ROSE

Jean Gaujard, Feyzin, France, assignor to Jackson & Perkins Company, Newark, N. Y.

Application May 5, 1937, Serial No. 140,978

1 Claim. (Cl. 47—61)

The present invention relates to a new and distinct variety of rose plant, originating from certain unnamed seedlings of the original Pernet-Ducher strain.

For a full understanding, it may be noted that when J. Pernet Ducher, a great and well known rose hybridizer, died in the year 1928, he left a large collection of unnamed seedlings of the pure Pernetiana race unmixed with other strains for development purposes, and the present variety is the result of a recombination by me of certain of these selected breeders.

The new variety is distinguished from the previous creations of Pernet-Ducher by the extraordinarily rich and brilliant color of the blooms, as yet unknown in roses. While it is practically impossible to describe this color in words because it does not exist in a true sense in standard charts, the accompanying drawing does illustrate the coloring as nearly as can be depicted.

So far as the foliage of the plant is concerned, this is typically Pernetiana, generally very similar to Souv. de Claudius Pernet foliage in color, serration and general effect. It differs from this foliage in that the leaflets are spaced farther apart, giving a slightly more sparse individual effect, and the thorns are not quite as numerous as they are on the Souv. de Claudius Pernet.

This new variety has been tested and rebudded over a long period of time on various understocks both in Europe and America and has always come true to original form.

The following is a detailed description of this new variety, reference to color according with the Ridgway's color chart:—

Parentage:

*Seed parent.*—Seedling of Pernet Ducher #197. Flower large, reddish orange, beautiful foliage.

*Pollen parent.*—Seedling of Jean Gaujard. Beautiful pointed bud, yellowish orange, very vigorous.

Classification:

*Botanic*—Pernetiana.

*Commercial.*—Hybrid Tea (according to A. R. S. classification).

*Flower*

Blooming habit:

*Location where observations were made.*—Gaujard Nurseries in Europe and Jackson & Perkins Nurseries in America.

Recurrent—continuous.

Bud:

*Size.*—Very large.

*Form.*—Ovoid; unaffected by wet or hot weather.

*Color.*—When sepals first divide—Plate III, Orange with wash of light greenish yellow, Plate V. When petals begin to unfurl—Plate III, Cadmium Orange. When half blown: inside of petals—Plate III, Cadmium Orange; reverse of petals—Plate III, Mikado Orange.

*Sepals.*—Smooth edge. Curl back when bud unfurls.

*Calyx.*—Shape — funnel. Size — broad. Aspect—smooth. No odor when rubbed.

*Peduncle.*—Length—medium. Aspect—rough. Color—Plate XXXI, Light Cress Green. Strength—bending.

*Opening.*—Bud opens well; is not affected by adverse conditions.

Bloom:

*Size.*—Very large; average size when fully expanded—4 to 5″.

*Borne.*—Singly.

*Stems.*—Long, normal strength.

*Form.*—Globular; retains its form to the end.

*Petalage.*—Very double (many petals and stamens hidden). Number of petals under normal conditions—100.

*Color*—Center of flower—Plate II, Flame Scarlet. Outer petals—Plate III, Mikado Orange. Base of petals (aiglet)—Plate IV, Apricot Yellow. Inside of petals—Plate III, Orange. Reverse of petals—Plate III, Deep Chrome. General tonality from a distance—Plate III, Orange.

*Variegations.*—None.

*Discoloration.*—No discoloration at end of first and second days. Third day — slightly lighter.

Petals:

*Texture.*—Thick; unaffected by wet or hot weather.

*Appearance.*—Inside—shiny; outside—satiny.

*Form*—Round.

*Arrangement.*—Imbricated (regularly arranged shingle-like). Petaloids in center — few, large.

*Persistence.*—Drop off cleanly.

*Fragrance.*—Moderate. Nature—Fruity (Russet apple).

*Lasting quality.*—On plant and as cut flower, very long.

Genital organs:

*Stamens, anthers.*—Medium side, few. Color—Plate IV, Apricot Yellow. Arrangement—mixed with petaloids.

*Stamens, filaments.*—Medium length. Color—Plate IV, Pinard Yellow.
*Pollen.*—Plate XVI, Napthalene Yellow.
*Styles.*—Loosely separated, uneven length; medium length, heavy.
*Stigmas.*—Plate XVI, Napthalene Yellow.
*Ovaries.*—Some protruding from calyx.

Fruit:
Variety is rarely fertile with its own pollen.
*Form.*—Ovoid.
*Aspect.*—Smooth.
*Color at maturity.*—Plate XIV, Hazel.
*Sepals.*—Caducous.

*Plant*

Form:
Bush.

Growth:
Medium, branching.

Foliage:
Generally five leaflets.
*Size.*—Large.
*Quantity.*—Abundant.
*Color.*—New foliage: upper side—Center Plate XVII, Hellebore Green—Edge Plate XIII, Madder Brown; under side—Center Plate XVII, Light Hellebore Green—Edge Plate XIII, Diamine Brown. Old foliage; upper side—Plate XXXI, Dark Cress Green; under side—Plate XXXI, Light Cress Green.
*Shape.*—Oval pointed.
*Texture.*—Upper side—glossy; under side—smooth. Ribs and veins—ordinary.
*Edge.*—Serrated. Serration—single, small.
Rachis.—Color—Plate XXXI, Light Cress Green. Under side—prickles.
*Stipules.*—Medium length, smooth.
*Disease resistance.*—Resistant.

Wood:
*New wood.*—Color—Plate XXXI, Light Cress Green. Bark—smooth.
*Old wood.*—Color—Plate XXXI, Dark Cress Green. Bark—rough.

Thorns (divided into thorns, prickles and short needles):
*Thorns.*—Quantity—on main stalks from base—ordinary; on laterals from stalk—few. Form—broad base, medium length, hooked downward. Color when young—Plate XIII, Vandyke Red. Position—irregular.
*Prickles.*—Quantity—on main stalks—few; on laterals—none. Color—Plate XIII, Vandyke Red.
*Short needles.*—None.

I claim:
A new and distinct variety of everblooming rose plant particularly useful for mass bedding, characterized as to novelty by the unusual and distinctive coloring of the flowers, substantially as shown and described.

JEAN GAUJARD.